United States Patent [19]
Senger et al.

[11] Patent Number: 5,111,799
[45] Date of Patent: May 12, 1992

[54] ESTROUS DETECTION SYSTEMS

[75] Inventors: Phillip L. Senger; Willard C. Becker, both of Pullman, Wash.

[73] Assignee: Washington State University Research Foundation, Inc., Pullman, Wash.

[21] Appl. No.: 502,032

[22] Filed: Mar. 28, 1990

[51] Int. Cl.⁵ .............................................. A61B 10/00
[52] U.S. Cl. ..................................... 128/738; 128/774
[58] Field of Search ............................. 128/738, 774; 364/413.12

[56] References Cited

U.S. PATENT DOCUMENTS

| | | | |
|---|---|---|---|
| 3,076,431 | 2/1960 | Rule et al. | 119/1 |
| 3,158,134 | 8/1963 | Larson | 119/1 |
| 3,205,857 | 4/1964 | Larson | 119/1 |
| 3,297,020 | 1/1967 | Mathiesen . | |
| 3,824,989 | 5/1973 | Horner . | |
| 3,844,273 | 10/1974 | Polson | 128/738 |
| 3,948,249 | 3/1975 | Ambrosini . | |
| 4,206,766 | 6/1980 | Bielka | 128/738 |
| 4,239,017 | 7/1979 | Schwarz | 118/656 |
| 4,247,758 | 11/1979 | Rodrian | 235/92 MS |
| 4,411,274 | 10/1983 | Wright | 128/738 |
| 4,455,610 | 2/1982 | Rodrian | 364/415 |
| 4,635,587 | 1/1987 | Leonardo | 128/738 |
| 4,696,258 | 9/1987 | Magrath | 128/738 |
| 4,846,106 | 7/1989 | Leonardo | 128/738 |
| 4,895,165 | 1/1990 | Blair | 128/738 |

FOREIGN PATENT DOCUMENTS 1189575  6/1985  Canada ................................ 128/738

OTHER PUBLICATIONS

Thompson, et al., Transducers for Capture of Activity Data, paper presented at 78th Annual Meeting of American Dairy Science Assn., Jun. 1983, Univ. Wisconsin.
Activity Monitor brochure, Dairy Equipment Co., Madison, Wis. 1984.

Primary Examiner—Ruth S. Smith
Assistant Examiner—Robert L. Nasser, Jr.
Attorney, Agent, or Firm—Wells, St. John & Roberts

[57] ABSTRACT

Disclosed is an apparatus for estrous detection, analysis and telemetric communication of a signal indicating estrus. The apparatus is specially adapted for surgical implantation on the hindquarters of cattle or other animals which exhibit selective standing heat behavior often termed standing to be mounted. The apparatus which is implanted under the hide of the animal, comprises a self contained power source, a force responsive sensor, a controller, a transmitter, an antenna, and a fluid-tight capsule which surrounds the other elements of the apparatus. The apparatus operates by sensing force applied during sustained mounting of an animal which is in estrus by another animal in the herd. The implantable apparatus analyzes the duration of mounting to discriminate standing heat mountings from shorter duration spurious mountings which routinely occur in cattle herds. The number of standing heat mountings which occur in a fixed period, for example 8 hours, are counted and the frequency is compared to a threshold which determines whether estrus should be indicated by transmitting a telemetric signal from the implanted apparatus. The telemetric signal is broadcast from the subcutaneous location to a receiver and suitable indicator from which the state of estrus can be perceived by the herdsman. The systems allow fully automated estrous detection and analysis to be performed. Also disclosed are methods for detecting, analyzing and signaling estrus in animals exhibiting standing heat behavior.

36 Claims, 6 Drawing Sheets

_FIG. 8_

_FIG. 9_

ESTROUS DETECTION SYSTEMS

TECHNICAL FIELD

The field of this invention is estrous detection and monitoring in cattle and other animals which exhibit certain mounting behavior which is estrus specific in duration, frequency or other detectable property.

BACKGROUND OF THE INVENTION

The artificial insemination of dairy cows and other domestic animals is an important procedure in the dairy and other livestock industries. Knowledge of the available time for breeding is also desired for herdsmen when natural breeding is planned. In many species of domesticated and wild animals the female animal must be inseminated during or shortly after a relatively brief period of sexual receptivity to achieve conception. This period of sexual receptivity is referred to alternatively as the estrous period, estrus, or heat.

In cattle, the estrous period occurs approximately every 21 days in nonpregnant females. Estrus in cattle lasts for a relatively short 12-24 hour period, during which time the cows must be inseminated in order to become pregnant. In modern dairy farming cows are typically inseminated artificially. In dairy cattle, pregnancy is necessary to bring about physiological changes which provide for the onset of milk production. After an initial pregnancy, dairy cows are preferably maintained pregnant to insure milk production. In beef cattle, control over the timing of pregnancy for the production of calves is very important, especially for range cattle. Lost time between calving is also of significant economic importance to beef cattle herdsmen.

It is known that cattle exhibit several behavioral and physiological characteristics which are specific to the estrous phase of their cycles, or which occur very near estrus. Physiological indications that an animal is in estrus include increased blood flow to the reproductive tract, changes in the impedance of reproductive tract fluids, elevated body temperature, and changes in blood hormone levels.

Behavior indications that cattle are in estrus include nervousness, increased physical activity and mobility, and increased vocalization (bawling). Cattle also exhibit certain behavior associated with mounting. During estrus there is an increased frequency of mounting of other cattle by the animal in heat. Another characteristic of estrus in cattle which is particularly important to this invention is that cows in heat will allow themselves to be mounted and remain mounted by other cattle. This behavior termed "standing to be mounted" is mating behavior exhibited by the cow in heat. Although cattle are mounted by other cattle at times outside of estrus, cows will maintain a relatively prolonged mounted standing posture during estrus. When cattle are not in estrus, they will not allow prolonged mounting by other cattle in the herd, and will walk out from under a cow or bull which is attempting to mount. This behavior has given rise to the term "standing heat" which indicates the period of actual estrus during which fertilization and conception can occur and the cow will stand to be mounted. During or approaching heat, cattle also place their chins on the hindquarters of the cow to determine if she will stand to be mounted. Standing to be mounted is also an indication of estrus in other animal species, such as sheep.

Prior attempts and systems for detection of estrus in cattle have not proven satisfactory. One approach involved placing pedometers on the legs of cows in order to measure increased movement and locomotive activity. This approach has proven to be inaccurate because increased physical activity can occur for a variety of reasons and can vary from one animal to another to a significant degree. Another prior attempt at detecting estrus in cattle involved the routine insertion of vaginal probes. The vaginal probes contained sensors which detected changes in the electrical resistivity of the vaginal mucus discharge. This method has proven undesirable due to the excessive manpower requirements for conducting the tests, and problems with maintaining sanitation and health of the cattle.

Several prior attempts to detect and signal the onset of estrus in cattle were premised upon the increased mounting behavior exhibited toward cows in heat. The Kamar heat mount detector and other similar units include the placement of special dye containers on the backs of cattle being monitored. When the animal in heat is mounted, the dye in the container is pressed from a reservoir into a viewing cylinder, thus providing a visible indicator of estrus. This technique results in a large number of false positives, apparently due to the spurious mounting of cows which are not in heat. Additionally, each device may be used only once and must be routinely and manually installed and removed from the cattle. This requires substantial amounts of time and effort on the part of herdsmen. Furthermore, the dye containers are difficult to attach on the hindquarters of cattle so that they will not be lost when the animal is mounted.

U.S. Pat. No. 4,206,766 discloses a mechanical device which is tripped by mounting behavior upon a cow wearing the device. This type of device is difficult to maintain in the desired position and requires examination of each cow wearing the device to determine if mounting has occurred. It is also prone to false tripping due to spurious mounting.

A somewhat different approach is shown in U.S. Pat. No. 3,824,989 to Horner et al. This patent shows a device which is mounted on a bull using a collar or harness and includes a marker which applies marking material to cows in heat. If the bull is not desired in the herd, too busy, or predisposed to certain cows, then the suitability and reliability of this approach decreases substantially. It also is subject to being dislodged from the bull and failure to provide a visually recognizable mark on the cows. This method also relies on the sexual interest or drive of the marking animal which is subject to substantial variation. Similar marking devices can also be installed on penal deviated bulls, penectomized bulls, estrogenized or androgenized cows.

Another technique which has been used is chalking of the tailheads of cows being monitored. This approach involves applying a grease crayon-like mark to the tailhead of the cow. Upon receiving mounting activity the mark disappears. This approach suffers from significant amounts of error, in part arising from the necessity of interpreting the presence or absence of the grease crayon from the animals hide. Other activities can cause the marking to disappear. This method also consumes substantial amounts of time since each cow being monitored must be marked daily. The application of the marking is further troublesome because the cows must be secured in a stanchion during application of the marking.

Another approach to cattle estrous detection is shown in U.S. Pat. No. 4,411,274 to Wright. The Wright patent discloses an electronic apparatus which is attached to the back of a female animal and transmits a signal when the animal is mounted by another animal. The maintenance of such a detector on the cow is difficult and subject to repeated loss of time and equipment.

A further approach to estrous detection is shown in U.S. Pat. No. 4,635,587 to Leonardo which discloses a saddle-like device which fits over the hindquarters of a cow. This device includes a sleeve for carrying an apparatus which includes both an electronic timer and indicator that are activated when the cow is mounted by another cow. The timer records the amount of time which has elapsed since the cow was mounted. A herdsman must visually identify the indicator and then read the mounting time information. It is also difficult to maintain the apparatus in the desired position on the cow.

U.S. Pat. No. 3,844,273 to Polsen discloses an apparatus which is attached to the back of an animal either by glue, straps, or a harness. Polsen's apparatus is also activated by the mounting of the animal, and a transmitter signal and timer are turned on. The transmitted signal is detected and the time information is then obtained from the unit.

Despite these numerous and long felt attempts, none of these prior art approaches has satisfactorily solved the problem of how to reliably and efficiently detect estrus, particularly in cattle. The approaches utilizing a detector which is connected to the animal being monitored for estrus have consistently suffered problems. These problems often are associated with the difficulty of maintaining the detection apparatus either on the leg or hindquarters of the animal. Prior to this time no one has solved this pervasive problem. The detecting apparatuses must remain attached regardless of the movement of the animal and contact with other animals and objects. This has often necessitated careful supervision and monitoring by the herdsman. Such monitoring is an additional chore not appreciated.

Many of the prior art devices also suffer problems associated with the need for routine monitoring by the herdsman. For example, timers must be read from the devices on the backs of individual animals in the patents to Leonardo and Polsen. Dye containers must be carefully inspected to discern whether mounting has occurred. The visual identification of detector status or information requires in most cases requires the careful inspection of the cow's detector. This consumes substantial amounts of time in large herds and often makes such estrous detection systems impractical, particularly on modern dairy farms where the number of herdsmen are minimized and milking and feeding work must be completed quickly. Thus it is apparent that automated estrous detection systems are needed in the livestock industries.

Another limitation of the prior art is the failure to continuously monitor estrus. Many of the prior techniques require routine maintenance or operation, such as installation of a new dye container, supplying new marking material, adjustment or repositioning of a mounted detector, or reading of the indicator to assess whether estrus has occurred. Such maintenance or operation often results in lapses in monitoring because of the unintended absence, replacement or removal of the detection device. Accordingly, there is a substantial problem associated with missing estrus because of the non-continuous operation of the prior art heat detection techniques.

A further problem of the prior art concerns the incorrect diagnosis of estrus for animals not truly in estrus. All of the prior art described hereinabove which relies upon mounting behavior fails to distinguish between non-estrous mounting and estrous mounting. Since cattle in a herd periodically mount one another as routine behavior, such as when the mounting cow is in heat, failure to discriminate cows in standing heat from those incidentally mounted can cause substantial losses in time and increased costs associated with artificially inseminating non-fertile cows. Erroneous estrous diagnosis and associated artificial insemination can also lead to removal of estrous monitoring devices, thus causing a later true estrus to not be identified. This in turn causes at least one cycle to be missed and places an increased burden on the herdsman to diagnose for conception or additional cycles can be lost. Thus it can be appreciated that false indications can be particularly disadvantageous and costly.

Because of limitations and inadequacies, such as indicated above, the prior art estrous detection systems have not been well received by the cattle or dairy industries. For these reasons visual observation of cow behavior continues to be the primary technique used to determine estrus in cattle. However, only about 50% of the cows displaying behavioral indications of estrus are detected by human visual monitoring. Of the cows selected by visual observation, about 10-30% are not actually in heat. The faulty diagnosis of heat typically results from the absence of the observer, infrequent or careless observation, or to a lesser extent, because of only subtle behavioral manifestations of heat. Because of the high rates of error in visual observation and diagnosis, there are very substantial opportunities for improving the detection of heat in cattle and providing increased productivity as a result of such detection.

There remains a strong need for accurate, reliable, timely and economical systems and detectors for diagnosing estrus in cattle and similar animals exhibiting standing heat behavior.

BRIEF DESCRIPTION OF THE DRAWINGS

Preferred embodiments of the invention are illustrated in the accompanying drawings which are briefly described below.

FIG. 7 is a schematic diagram showing preferred electronic components of the apparatus of FIG. 1 and other parts of a preferred estrous detection and analysis system made in accordance with this invention.

DETAILED DESCRIPTION OF THE PREFERRED EMBODIMENTS

This disclosure of the invention is submitted in furtherance of the constitutional purposes of the Patent Laws "to promote the progress of science and useful arts" (Article 1, Section 8).

FIGS. 1-5 show a preferred estrous detection and signaling apparatus 10 according to this invention. Apparatus 10 includes an outer capsule 30 and an internal assembly 33. The internal assembly is preferably completely encapsulated within capsule 30. The capsule 30 provides a fluid-tight enclosure to isolate the various components of the internal assembly from the body fluids of the cow or other female animal in which apparatus 10 is subcutaneously implanted. The capsule 30 is preferably made of a flexible and resilient material which is tissue compatible in the animal species of desired use. Surgical grade silicone rubber is a preferred material of construction for capsule 30. Other tissue compatible surgical grade polymer materials are also expected to be satisfactory. Relatively elastic materials are preferred.

The outer surfaces of apparatus 10 advantageously include an upper convex surface 15 and a lower concave surface 25. The upper convex surface defines a force receiving dome area 16 which is adapted to deform in response to force applied to the apparatus. Sloping areas 18 extend downwardly and outwardly from the dome area 16 to the side edges 20 and end edges 21 of the capsule. The bottom surface 25 is concave approximately about a longitudinal axis extending between the end edges 21. The bottom surface extends laterally between the side edges 20. The corners defined at end edges 21 and side edges 20 are provided with curved radii to reduce the risk of irritation when the apparatus is implanted beneath the hide.

The outer configuration of the capsule is specifically adapted to both distribute and focus the applied forces associated with the mounted behavior of standing heat. The lower portions of the capsule are adapted to evenly distribute weight across the base or bottom surface 25. The side edges extend downwardly to provide initial contact or conformation about a curved supporting anatomical structure of the cow or other animal, such as a vertebra (see FIG. 6).

The outer shape of the apparatus is also specifically adapted to concentrate forces applied to the upper portions of the apparatus at the top or dome portion 16. This concentration of applied force at the dome causes the dome to more readily deform under the applied load. The domed shape is also advantageous in providing a resilient structural shape which returns after deformation and allows for a relatively long life of compressive deformations due to mounting of the implanted animal.

Figure 1:
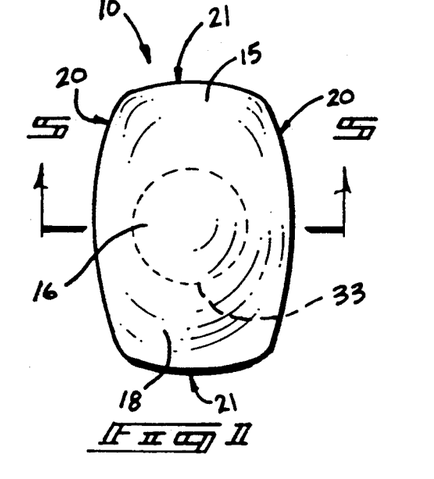
FIG. 1 is the top plan view of a preferred embodiment of subcutaneously implantable estrous detection apparatus made in accordance with this invention.
Figures 2, 4, 5:
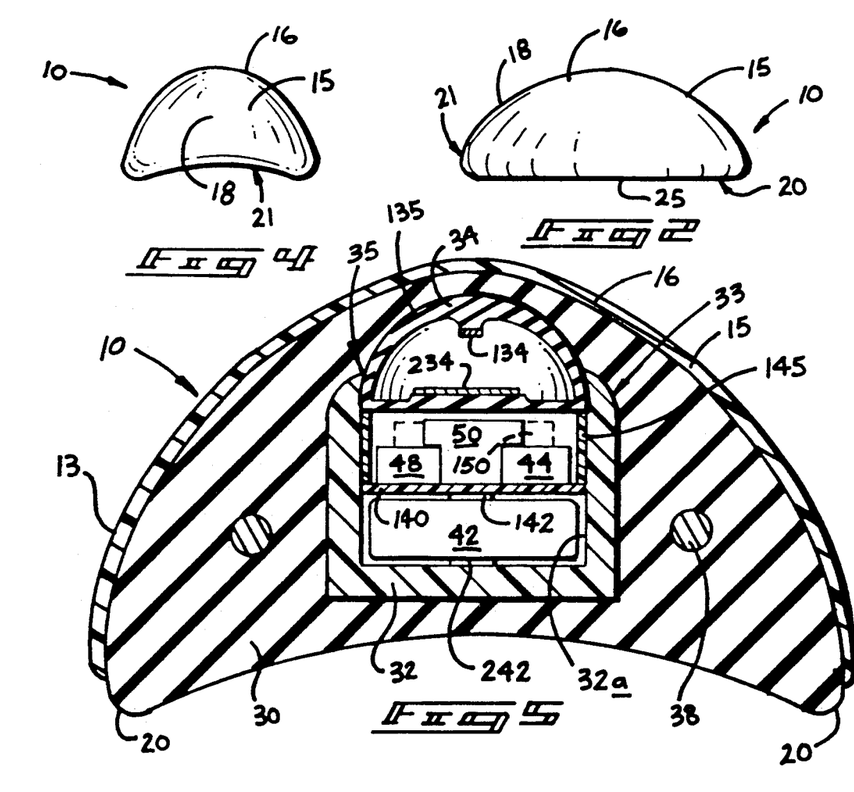
FIG. 2 is a side elevational view of the apparatus shown in FIG. 1.
FIG. 4 is a front elevational view of the apparatus shown in FIG. 1.
FIG. 5 is a cross-sectional view of the implantable apparatus taken along line 5—5 of FIG. 1.
Figure 2:
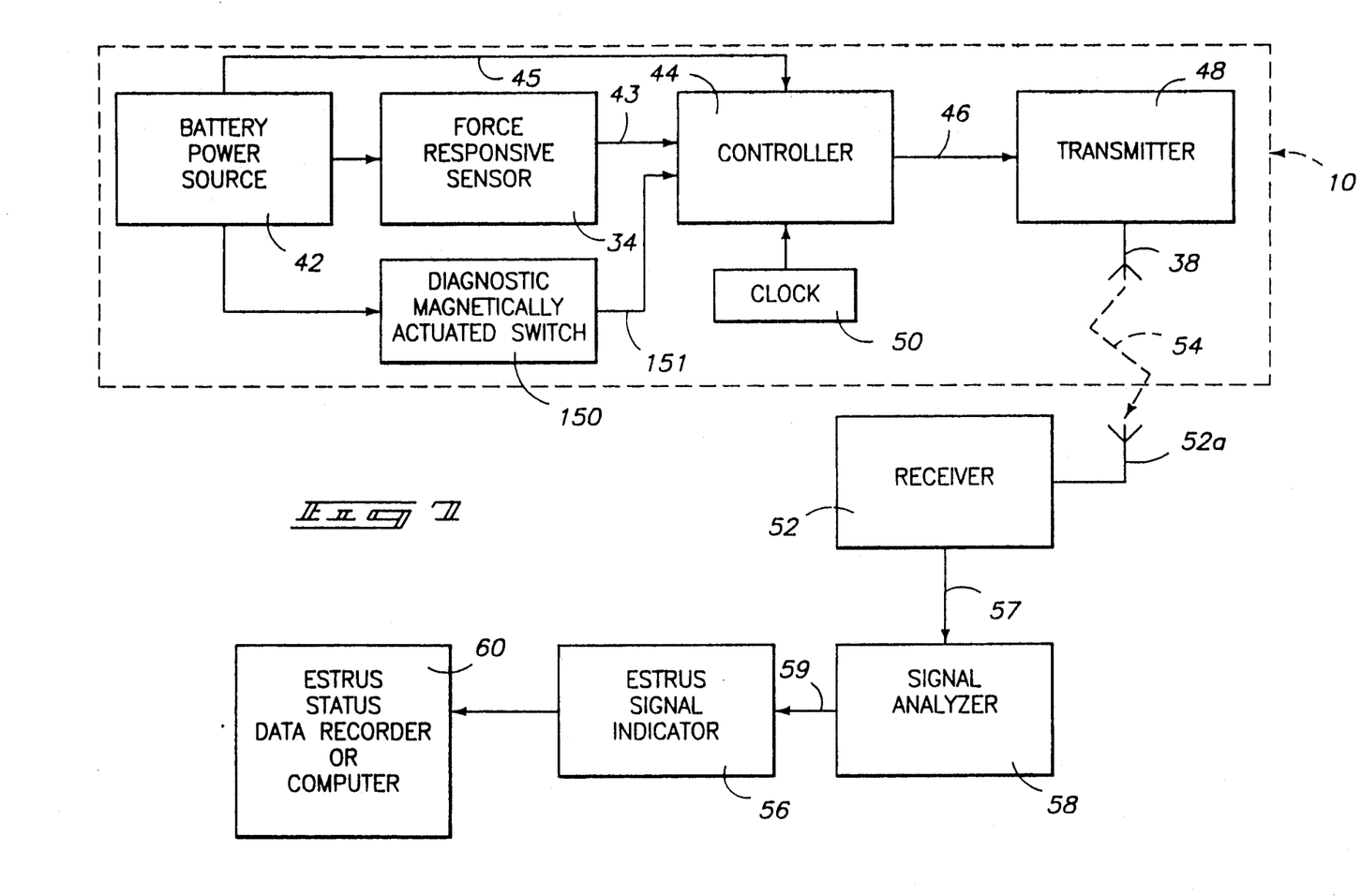
Figure 3:
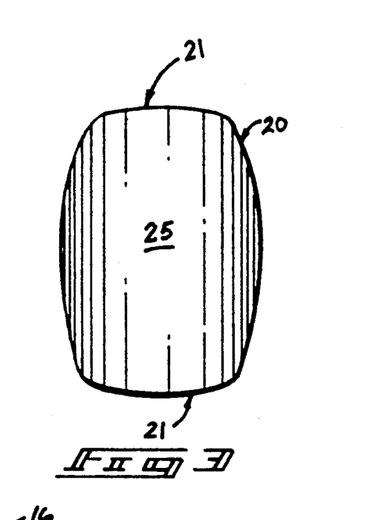
FIG. 3 is the bottom plan view of the apparatus shown in FIG. 1.

The outer upper surface 15 of the capsule is advantageously provided with an attachment layer or tissue connection means 13. The attachment or connection layer is advantageously provided over at least the domed upper portion of the capsule. More preferably, the attachment means is provided over nearly the entire upper convex surface, as shown in FIG. 5. The attachment means is preferably made of a porous tissue compatible material. Surgical reinforcement panels made from a number of suitable mesh or other reticulated materials and preferred. The mesh or other material is preferably made from a tissue compatible polymer material. One brand of suitable material is proxplast commonly used in the veterinary medicine for surgical reinforcement of tissue.

Figure 6:
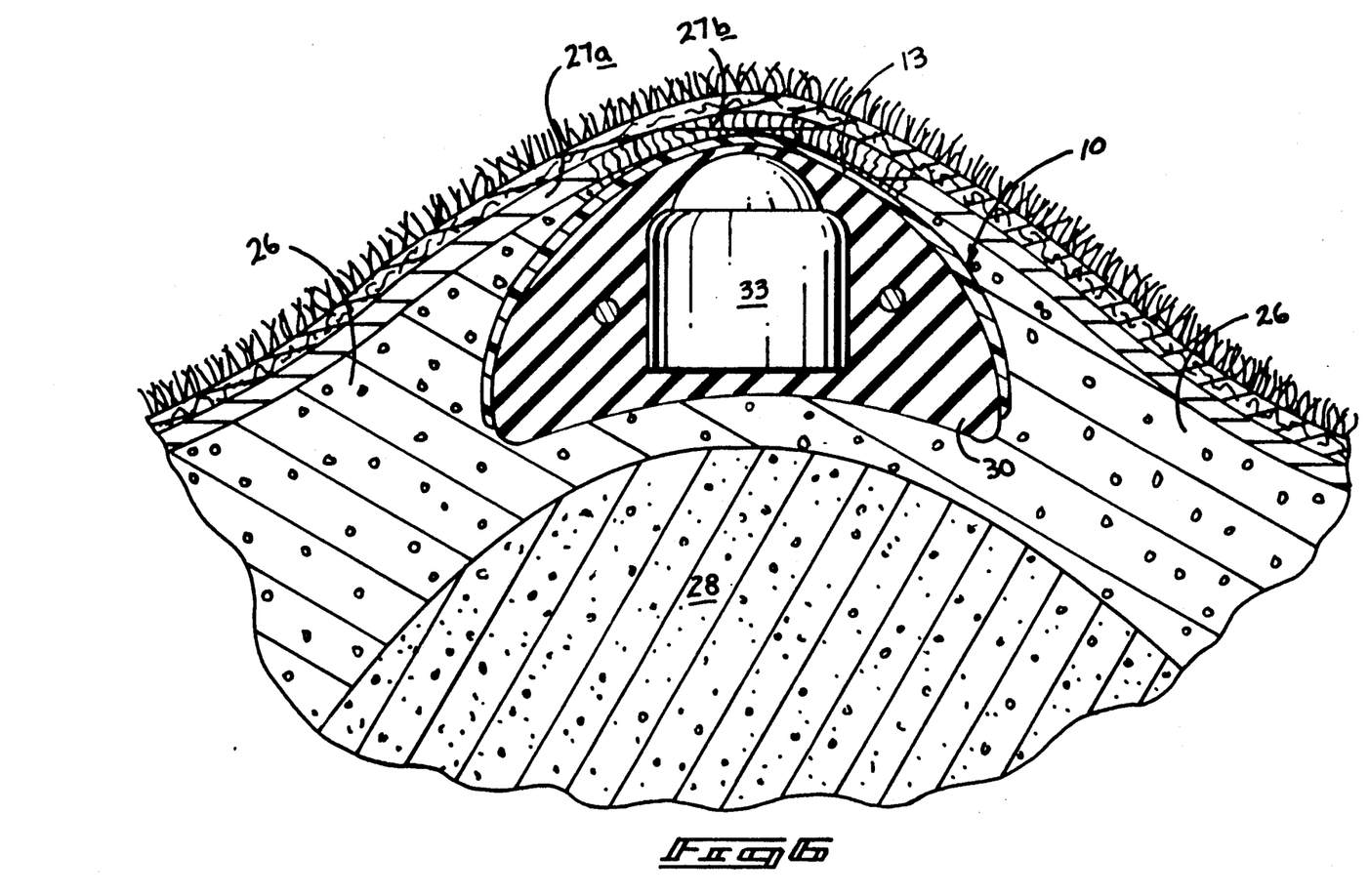
FIG. 6 is a diagrammatic cross-sectional view showing the apparatus of FIG. 1 as it might be implanted in upper rear portions of a cow.

FIG. 6 indicates that the attachment or connection means 13 is provided in order to help develop tissue growth 27b between the inside layer 27a of the hide 27 and the capsule to thereby aid in the location of the apparatus under the hide. The attachment of the apparatus to the hide also serves to facilitate removal of the apparatus when the animal is slaughtered. The hide attachment means will cause the estrous apparatus 10 to stay with the hide during skinning. This will eliminate potential problems associated with missing the apparatus and having it contaminate the meat butchered from the animals implanted with the apparatus. The apparatus can be easily scraped from the inside of the hide during the initial cleaning steps for processing the hide, such as for leather.

FIG. 5 shows that the capsule 30 is advantageously used to support a transmission antenna 38. Antenna 38 is made from a suitable electrically conductive material, such as copper or aluminum wire. Antenna 38 is preferably molded into the capsule 30 during manufacture. Antenna 38 extends about the perimeter of the capsule. It is advantageously enclosed within the capsule layer outside of the internal assembly 33. FIG. 5 also shows that internal assembly 33 is advantageously assembled in a support shell 32. The internal assembly support shell 32 can be made in a variety of suitable shapes. As shown the support shell is provided as an approximately cylindrical receptacle 32a. Alternatively, the internal assembly can be integrally connected by molding in epoxy or other suitable material. The upper end of support shell 32 is provided with an opening 35 through which components of the internal assembly are installed into the support receptacle. The upper end of the support shell near the opening is preferably formed to a relatively smaller diameter constriction to define the mouth of opening 35. The constricted mouth of opening 35 is adapted to connect or mount a force responsive sensor or switch 34. Support 32 is advantageously made from a material which is strong, lightweight, and either or both tissue compatible or resistant to corrosion by body fluids. Epoxy resins are suitable and preferred, although many other suitable materials will also clearly be appropriate.

The force responsive sensor 34 is preferably a force actuated switch having a first or movable contact 134, and a second or stationary contact 234. Electrical wires or other conductors (not shown) are connected to the first and second contacts. The contacts are made of suitable electrically conductive materials to conduct electricity when the dome is compressed sufficiently to bring the movable contact 134 into physical and electrical contact with the second or stationary contact 234. Mounting force sensor 34 advantageously includes a dome shaped upper wall 135 which deforms under the weight of a mounting animal along with the upper dome portions of the enclosing capsule 30.

The force responsive sensor is preferably made of a deformable resilient material, such natural or synthetic rubber and a myriad of other similar materials. The force responsive sensor advantageously serves as a plug or cap to close the upper end of the support shell receptacle 32a. The constricted upper edge of the opening 35 aids in retaining the sensor in place.

The interior compartment of the support shell 32a is advantageously adapted to hold a self-contained electrical power supply 42, such as a battery. Battery 42 is preferably a long life battery with relatively flat discharge characteristics, to allow the implantable estrous detector 10 to serve for several years at minimum. A suitable battery is a 3.5 volt lithium cell. The battery is contacted by upper and lower battery contacts 142 and 242, respectively. Battery contacts 142 and 242 are connected to wires or other suitable electrical conductors (not shown) to conduct current to the force responsive load switch 34, and to other electronic components stored in compartment 40.

Electrical components are connected to the remaining portions of the internal assembly using a partition wall 140. Partition wall 140 also mounts the first battery contact 142. Partition wall 140 can be a printed circuit board or merely a suitable supporting piece. A spacer sleeve 145 extends downwardly from the sensor 34 to hold the partition wall 140 downwardly to develop good contacts against the battery. A controller 44, transmitter 48, and clock 50 are mounted upon the upper side of partition wall 140. An optional diagnostic switch 150 is shown in phantom and described below.

FIG. 7 schematically shows the preferred electronics used in estrous detection apparatus 10. The battery 42 supplies electrical power to the force responsive sensor 34. In the preferred embodiment shown, the force responsive sensor functions as a switch to complete a circuit and produce a mounting event signal 43 which is communicated to controller 44. The apparatus can also optionally be provided with a diagnostic magnetically actuated switch 150 which switches power to the controller 44 via a test signal 151 in a manner the same as load switch or other force responsive sensor 34. Controller 44 is electrically connected to receive electrical power directly from battery 42 through power supply conductors 45 which are not switched by sensor 34, thereby allowing independent operation of the controller at suitable times as described hereinafter.

Controller 44 either includes an internal clock or is provided with clock information from an external clock 50 which is communicated to the analyzers, counters or other appropriate circuitry using clocked signals. The controller outputs a transmitter activation signal 46 to transmitter 48. Transmitter 48 selectively outputs a telemetric signal 54 which is indicative that the animal has experienced behavior indicating estrus. The telemetric signal 54 is communicated to the transmitter broadcast antenna 38 from which it is broadcast to a receiver 52 unit via receiver antenna 52a.

Figure 7A:
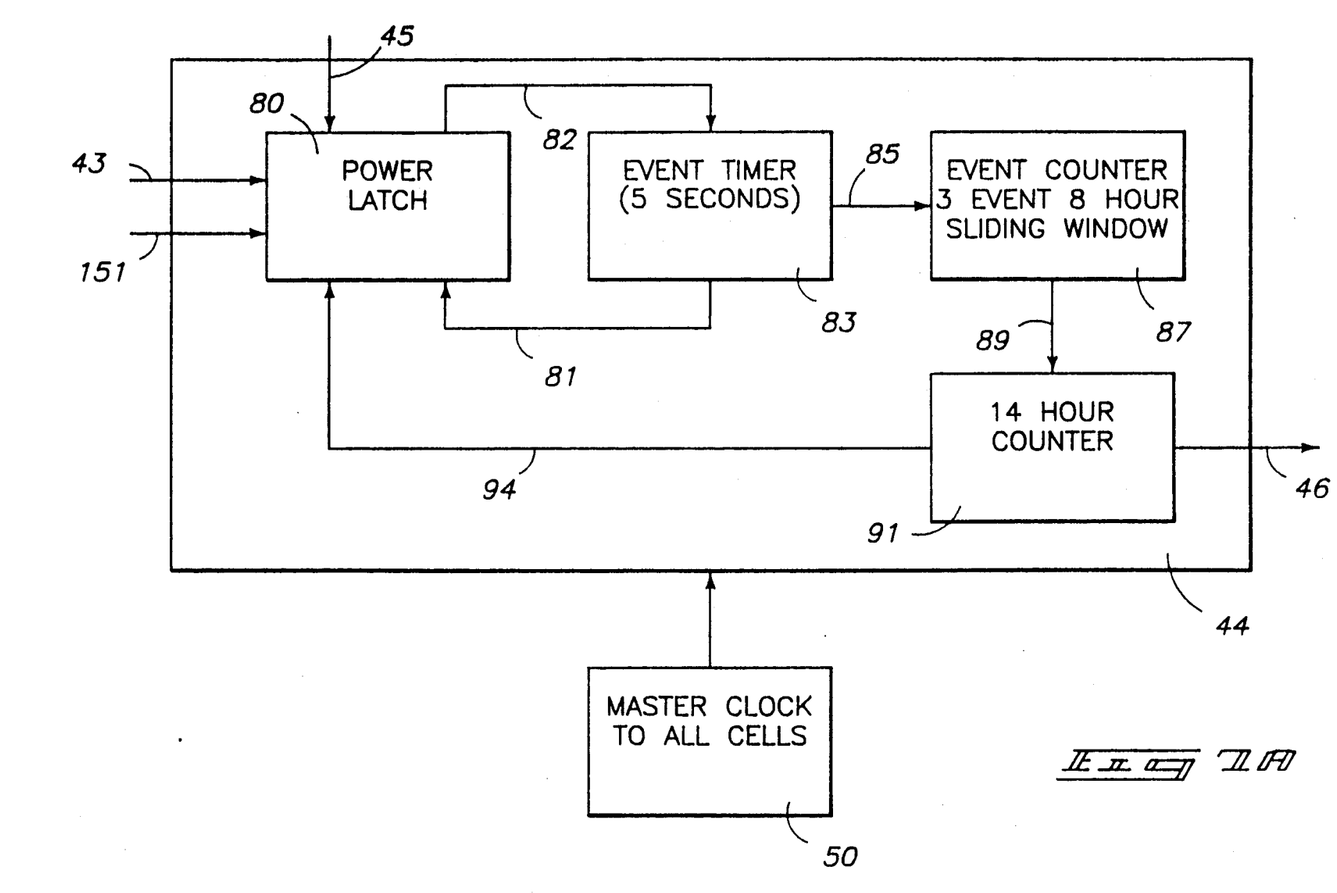
FIG. 7A is a schematic diagram showing additional detail of a preferred form of the controller pictured in FIG. 7.

FIG. 7A schematically shows the preferred analyzing circuits and related parts and functions of controller 44. The specific components used to implement these functions can be selected from a number of suitable digital devices incorporating suitable counters, gates and other logical devices. The mounting event signal 43 is input to a latch 80 which acts as a multiple input control relay. The input impedance of mounting event signal 43 to latch 80 is made relatively high to conserve electrical energy of the battery 42. The power latch outputs a power enable signal 82 which initiates the operation of an event timer 83. The event timer acts as a standing heat mounting event analyzer to selectively discriminate only those mountings which are indicative of standing heat. The event timer 83 is a counter which receives a clock signal from clock 50 and compares the counted duration of the power enable signal (and associated mounting event signal) and compares the mounting event duration to a suitable predetermined standing heat mounting event duration threshold. The standing heat event threshold discriminates between mounting events of short duration, herein called spurious mounting events, and mounting events of duration longer than the threshold which are classified as standing heat events. The preferred standing heating event threshold is approximately 5 seconds. Mounting events which last for approximately 5 seconds or longer are standing heat events which result in the output of a standing heat event signal 85 which is communicated to a standing heat event counter 87. The standing heat analyzer 83 also communicates a power enable latching signal 81 back to the latch to maintain power for operation of the controller during periods of analysis even though a mounting event is not in progress.

The standing heat event counter 87 serves as an estrous analyzer. The estrous analyzer counts the number of standing heat events which occur during a standing heat analysis period. A preferred standing heat event analysis is 8 hours. Somewhat shorter or longer standing heat event analysis periods are alternatively possible. The standing heat event counter 87 compares the number of standing heat events occuring within the standing heat event analysis period. The number of counted standing heat events is compared to a predetermined standing heat event frequency threshold. A preferred standing heat event frequency threshold is 3 standing heat events in an 8 hour standing heat analysis period. Upon the occurrence of 3 standing heat events within the counting period, such as 8 hours, then the standing heat event counter outputs an estrous analyzer output signal 89.

The estrous analyzer output signal 89 is preferably output through a transmitter control subcircuit 91. The transmit control subcircuit is preferably a counter. Counter 91 is activated when the estrous analyzer output signal 89 is active. The transmitter control subcircuit outputs the transmitter activiation signal 46 during a predetermined transmission period. The counter 91 counts the period of transmission and compares it against the predetermined transmission period. When the predetermined transmission period has been completed then the counter 91 disables the transmitter activation signal 46. The counter 91 also provides a power disable signal 94 which is input to power latch 80 thus turning the power to the controller 44 off until the next activation by a mounting event signal 43 from sensor 34.

FIG. 7 shows that the telemetric estrous indicating signal 54 is communicated telemetrically from antenna 38 to one or more receivers 52. Receiver 52 can be selected from many suitable types dependent upon the transmitter 48 used in the implantable apparatus 10. The transmitter is preferably a frequency modulated radio transmitter having a frequency in the very high frequency range (30-300 MHz), such as 150-160 MHz. The output telemetric signal from transmitter 48 is preferably a pulsed emission at a suitable transmission reoccurrence frequency, such as once every 5 seconds. A variety of commercially available miniaturized transmitters can be used coupled with a suitable means for pulsing the intensity of the output signal.

Similarly, a variety of suitable radio receivers 54 can be used to detect the signal output from the transmitter 48. The receiver is suitably tuned to receive the telemetric signal from transmitter 48. The transmitters in different animals can be tuned to different frequencies to achieve differentiation between different animals and the detection of estrus for each. Alternatively, it is possible to encode information in each transmitter emission pulse which indicates the transmitter producing the signal. The receiver 52 is preferably connected to output the received signal 57 to a suitable signal analyzer 58. Signal analyzer 58 can be as simple as a relay (not shown) which trips upon receipt of a sufficiently powerful signal from the receiver 52. Alternatively, it can be selected to decode information which is encoded in the transmitter telemetric signal received by receiver 52.

The signal analyzer 58 is preferably connected to output an estrous signal 59 to any desired estrous signal indicator 56. The estrous signal indicator can be a light emitting device for visual indication, an auditory emission device, a combination of both, or some other appropriate indicator. The receiver 52 or signal analyzer 58 are advantageous coupled to suitable latching circuitry (not shown) to provide continued activation of the estrous signal indicator 56. The estrous signal indicator can be appropriately reset by a reset switch (not shown), or automatically reset after a predetermined time period.

FIG. 7 further indicates that preferred systems according to this invention can advantageously include an estrous status data recorder 60. Estrous status data recorder 60 can advantageously be a multipurpose computer, such as a personal computer, with appropriate input output adapters and data acquisition software. The information about estrous status can be automatically compiled from a number of receivers and analyzed by computer 60 to provide a printout of animals needing insemination. Analysis of estrous days, frequency, pregnancy and other relevant information can be accomplished in unit 60 to increase information to the herdsman. The estrous and pregnancy information can be combined with more generally information on feeding and herd management.

Figure 8:
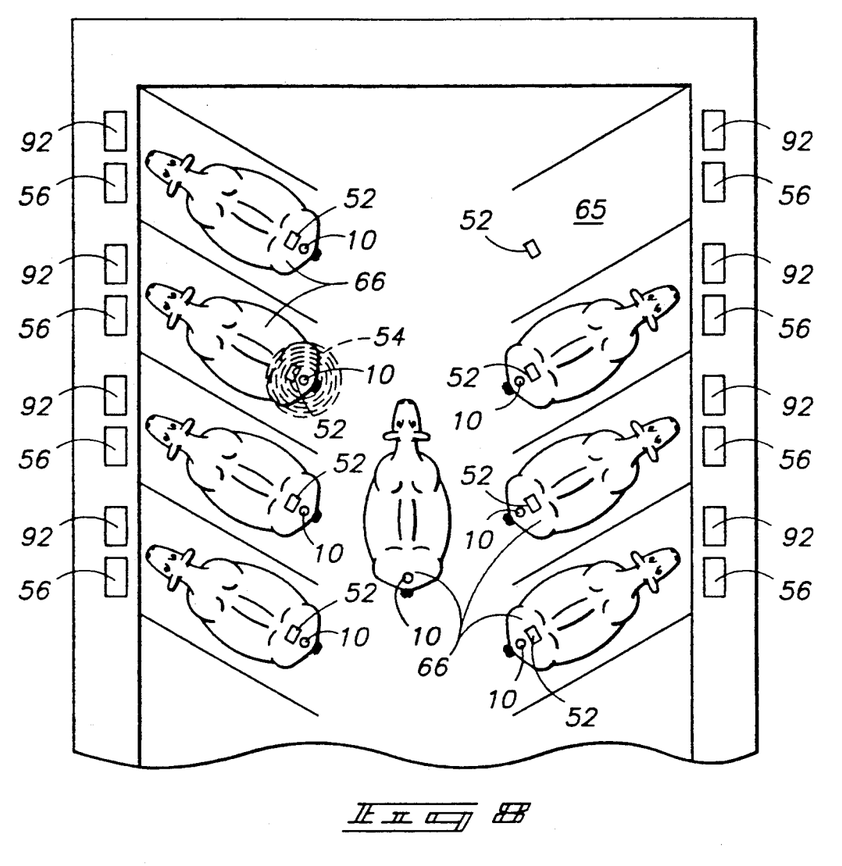
FIG. 8 shows additional features of a preferred automatic cattle estrous detection system according to this invention.

FIG. 8 shows a preferred automated estrous detection and signaling system according to this invention. FIG. 8 generally shows a portion of a feeding station for dairy cattle. The cattle are positioned in stalls 65. At their heads are automated feeding machines 92 and estrous signal indicators 56 which advantageously include a light which is selectively turned on to indicate estrus. The data collection unit 60 (FIG. 7) and automated feeding machines 92 can be interconnected or integrated to store and administer information about the particular cows. Suspended above the hindquarters of cows 66 are the receivers 52. The receivers are either arranged to selectively receive from the subjacent cow, or the frequencies of the various transmitter and receiver units can vary between animals to eliminate mistaken reception of an estrous signal from an associated animal. The cattle have surgically implanted estrous detection and signaling units 10 at their hindquarters, which if activated send a signal 54 to the appropriate receiver 52.

Figure 9:
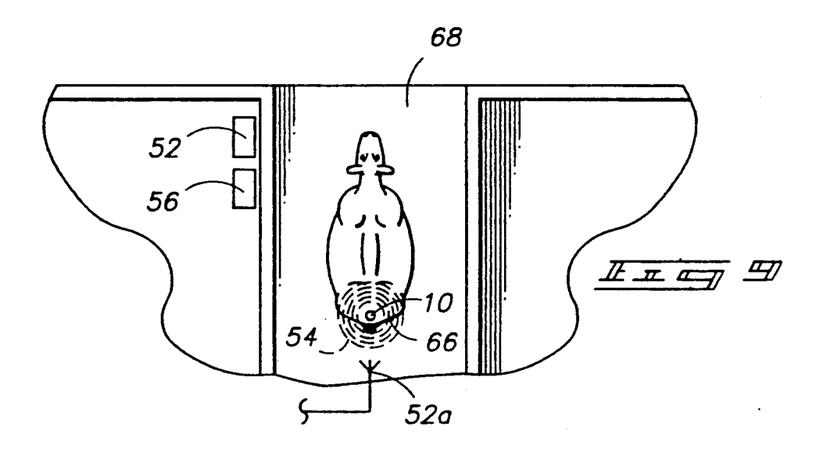
FIG. 9 shows features of an alternative automatic cattle estrous detection system according to this invention.

FIG. 9 shows another preferred alternative system according to this invention. The system of FIG. 9 includes a chute 68 through which cow 66 passes, such as in progress to a milking parlor or a computorized feeding station as shown in FIG. 8. Adjacent to the chute is a receiver 52 and an estrous signal indicator 56. The receiver 52 can be laterally positioned relative to the chute or positioned above the chute, such as by placing a remote receiving antenna 52a above the centerline of the chute. The receiving antenna 52a receives any estrous-indicating telemetric signal 54 emitted from the surgically implanted subcutaneous heat detection and signaling apparatus 10. A herdsman can be positioned adjacent to the chute to record the cow information. Alternatively, where the telemetric signal is encoded with cow-specific information, the received signal is analyzed and the information can be appropriately input to the computer 60 for completely automated recording and indication.

A further alternative receiver and indicator configuration includes a hand-held unit incorporating the receiver 52, any signal analyzer 58 and estrous signal indicator 56. The hand-held unit can be used for field identification of animals in heat.

The invention further includes methods for obtaining information indicative of estrus in a female animal which exhibits standing heat behavior. Standing heat behavior as used herein refers to behavior which is selectively associated with true estrus. In more particular terms, standing heat behavior is the behavior which is exhibited by a cow or other animal which demonstrates a willingness for standing to be mounted. This willingness causes a discernible longer period of mounting to occur than is experienced by spurious mounting when the cow or other animal is not in heat.

Figure 10:
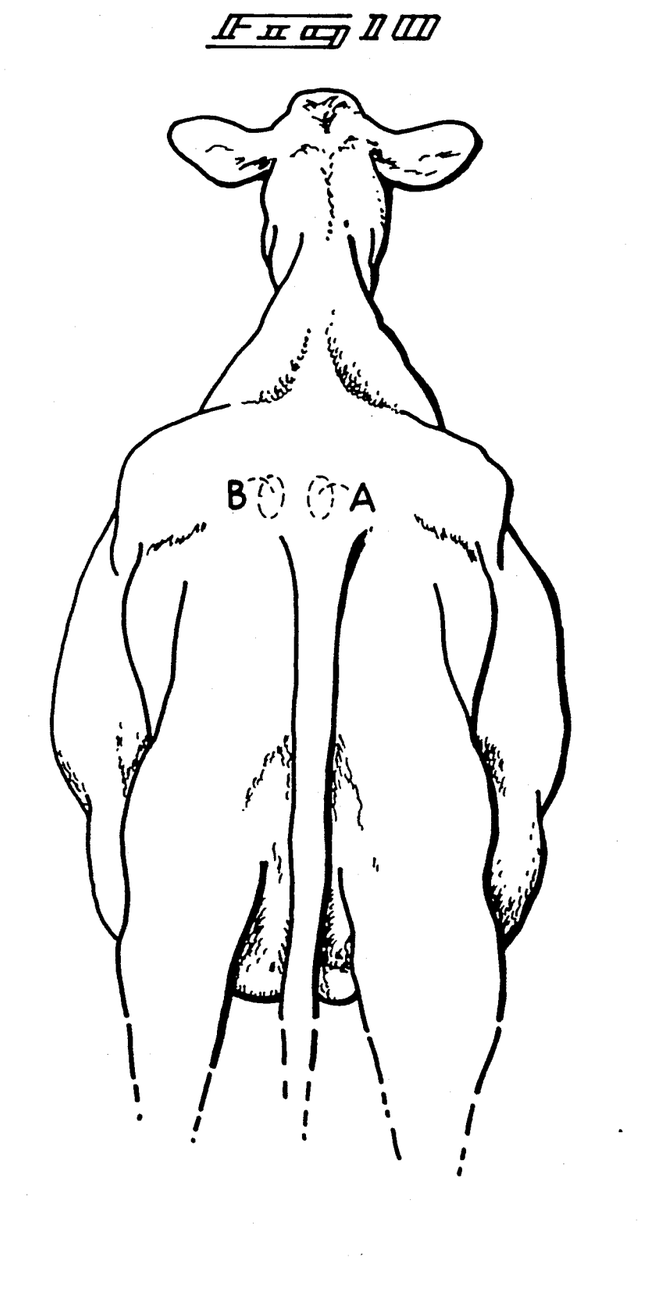
FIG. 10 shows a rear view of a cow and appropriate locations for implantation of preferred estrous detection and signaling units according to this invention.

Novel methods according to this invention involve obtaining or constructing a suitable apparatus for detecting, analyzing and signaling estrus, such as apparatus 10 as described hereinabove. The subcutaneously implantable apparatus 10 is surgically implanted into the hindquarters of the animal at a suitable location. Preferred locations are those regions of typical mutual contact between animals during mounting. Preferred locations are also defined by anatomical considerations of the implanted animal to provide adequate support for the apparatus and a minimum of inconvenience to the animal. FIG. 10 shows two suitable locations A and B for implantation of the apparatus 10 near the tail head region. One location A is above the sacrum and the other B is laterally offset from near the juncture of the sacrum and first caudal vertebra. Other suitable locations may also be possible.

FIG. 6 illustrates the approximate location of apparatus 10 after implantation over the vertebra 28. The unit is beneath the hide and adhered thereto by tissue ingrowth 27b with the connection layer 13. Adipose tissue 26 surrounds and cushions the implanted subcutaneous detector and signaling device.

The surgical implantation of the subcutaneously implantable estrous detection apparatus 10 is preferably accomplished by cutting an incision near the desired location of implantation. The incision need only be of sufficient size to allow insertion of apparatus 10 beneath the skin. The self-contained apparatus is then inserted through the incision and manipulated as needed to achieve the desired position relative to the cow's anatomy. The incision is thereafter closed, such as by using suture or staples. The apparatus 10 is preferably implanted a sufficient period in advance of expected estrus so that healing can occur prior to mounting behavior.

The operability of the implanted apparatus 10 can be checked by passing a magnet near to the implanted location. The magnet closes the magnetic reed switch or other diagnostic sensor 150. This is sustained for at least 3 periods of 5 seconds each to instigate transmission of the telemetric signal. If no signal is received then a new unit is implanted.

Methods of this invention further include exposing the implanted animal to other members of the herd to thereby provide the possibility for standing heat mounting behavior. If the animal is in true estrus, standing heat, then she will stand to be mounted. The standing to be mounted behavior will be exhibited for approximately 8-24 hours. During this period a plurality of standing heat mountings occur, thus causing the force responsive sensor 34 to be closed at the first and second contacts 134 and 234. The closing of the contacts 134 and 234 causes the controller to sense mounting events. The standing heat event analyzer 83 discriminates between relatively short duration mounts which do not reliably indicate standing to be mounted. If mountings of duration beyond the standing heat event duration threshold, such as 5 seconds, occur then the quantity of such standing heat mountings are counted by the estrous analyzer 87. The estrous analyzer is preferably constructed to count over a sliding or floating 8 hour period. If during any 8 hour period three standing heat mounting events are counted then the estrous analyzer outputs signal 89 which causes the transmitter activation signal 46 to be output from controller 44. Signaal 89 also starts the 14 hour or other appropriate transmission period running using counter 91. This amount of transmission time is sufficient to detect estrus in dairy cattle because milking occurs 2 or 3 times daily and the cows are preferably monitored for transmission during milking or in route to or from milking. When the period of estrous or herd management practices indicate shorter or longer transmission times, then such variations can easily be provided in both the electronic structure and programming needed to effectuate varying standing heat event threshold frequencies and transmission times.

The methods of this invention further include bringing the implanted animal into proximity with a suitable receiver for receiving the telemetric signal 54 which is indicative that the animal has experienced standing heat behavior and estrus. The methods further involve receiving the telemetric signal from the implanted apparatus. The receiver 52 or signal analyzer 58 then processes the received telemetric signal to produce an estrous signal which is appropriately transformed to provide a perceivable indication to the herdsman that a particular animal is predicted to be in estrus. The methods can further be defined to include artificially inseminating the cows or other animals in response to the detected estrous information.

The apparatus 10 according to this invention is advantageously made by selecting or making a suitable support, such as shell 32. Shell 32 is preferably molded or fabricated from an epoxy resin. The battery, other components described hereinabove, and connecting wires are then assembled together and placed into the shell 32. The shell is closed by inserting the force switch 34 into the top of the shell. Alternatively, the internal assembly components can be molded into an integrated unit to form a shell and integrated assembly. This can be done using epoxy or other suitable material. The resulting internal assembly 33 is then advantageously encapsulated with a protective, fluid-tight layer, such as capsule layer 30. The capsule layer is formed to provide flexibility and sensitivity for the force sensing head of the internal assembly. The encapsulating outer capsule 30 is preferably formed to provide a flexible and resilient structure. The encapsulation can advantageously be accomplished by molding a surgical grade silicone rubber about the internal assembly. The transmission antenna 38 is preferably positioned during the molding or other forming of the capsule so as to be fully enclosed within the capsule wall.

Remaining components of the system can be selected from or constructed similar to commercially available electronic receivers, signal analyzers, and data storage and analysis equipment. Any suitable indicator light or alarm can be used as estrous indicator 56.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. A subcutaneously implantable apparatus for detecting and signaling estrus in a female animal which exhibits standing heat behavior, comprising:

a substantially fluid-tight capsule made of tissue compatible material suitable for surgical subcutaneous implanation in said animal;

a tissue connector connected to the capsule for aiding in attachment of the apparatus to tissue in said animal to thereby assist in maintaining the apparatus in a desired location under the hide of the animal;

a self-contained electrical power source mounted within the capsule;

a force responsive sensor connected to the capsule for detecting force applied thereto;

a controller mounted within the capsule and connected to receive electrical power from the self-contained electrical power source; said controller being connected to receive information from the force responsive sensor which is indicative of application of force to the force responsive sensor; said controller being capable of producing a transmission activation signal;

a transmitter mounted within said capsule and connected to receive electrical power from said self-contained electrical power source; said transmitter being capable of producing a telemetric signal which is capable of broadcast through the hide of said animal when the apparatus is implanted; said transmitter being connected to receive said transmission activation signal from the controller to control production of the telemetric signal by the transmitter; and an antenna connected to the capsule and electrically connected to receive the telemetric signal from said transmitter and to broadcast the telemetric signal.

2. An apparatus according to claim 1 wherein said controller includes a standing heat analyzer for analyzing and discriminating standing heat events from spurious mounting events.

3. An apparatus according to claim 1 wherein said controller includes a standing heat analyzer for analyzing and discriminating standing heat events from spurious mounting events; said standing heat analyzer comprising means for comparing the duration of force detected by the force responsive sensor against a predetermined mounting event duration threshold.

4. An apparatus according to claim 1 wherein said controller includes a standing heat analyzer for analyzing and discriminating standing heat events from spurious mounting events; said standing heat analyzer comprising means for measuring duration of force detected by the force responsive sensor to determine mounting event duration and comparing the mounting event duration against a predetermined mounting event duration threshold; said standing heat analyzer being constructed to identify mounting events having a mounting event duration of approximately 5 seconds or longer as standing heat events.

5. An apparatus according to claim 1 wherein said controller includes an estrous analyzer for counting standing heat events to control production of said transmission activation signal.

6. An apparatus according to claim 1 wherein said controller includes an estrous analyzer; said estrous analyzer including means for counting a plurality of standing heat events and comparing frequency of standing heat events against a predetermined standing heat event frequency threshold, to control production of said transmission activation signal.

7. An apparatus according to claim 1 wherein said controller includes an estrous analyzer; said estrous analyzer including means for counting a plurality of standing heat events and comparing frequency of standing heat events against a predetermined standing heat event frequency threshold, to control production of said transmission activation signal; said estrous analyzer being constructed to produce a transmission activation signal if at least 3 standing heat events occur within an 8 hour period.

8. An apparatus according to claim 1 wherein said controller includes:
a standing heat analyzer for analyzing and discriminating standing heat events from spurious mounting events; and
an estrous analyzer for counting standing heat events to control production of said transmission activation signal.

9. An apparatus according to claim 1 wherein said controller includes:
a standing heat analyzer for analyzing and discriminating standing heat events from spurious mounting events; said standing heat analyzer comprising means for comparing the duration of force detected by the force responsive sensor against a predetermined mounting event duration threshold;
an estrous analyzer; said estrous analyzer including means for counting a plurality of standing heat events and comparing frequency of standing heat events against a predetermined standing heat event frequency threshold, to control production of said transmission activation signal.

10. An apparatus according to claim 1 wherein said controller includes:
a standing heat analyzer for analyzing and discriminating standing heat events from spurious mounting events; said standing heat analyzer comprising means for comparing the duration of force detected by the force responsive sensor against a predetermined mounting event duration threshold; said standing heat analyzer being constructed to identify mounting events having a mounting event duration of approximately 5 seconds or longer as standing heat events;
an estrous analyzer; said estrous analyzer including means for counting a plurality of standing heat events and comparing frequency of standing heat events against a predetermined standing heat event frequency threshold, to control production of said transmission activation signal; said estrous analyzer being constructed to produce a transmission activation signal if at least 3 standing heat events occur within an 8 hour period.

11. An apparatus according to claim 1 wherein said controller comprises means for producing a transmission activation signal for a predetermined transmission period and means for automatically resetting and ceasing production of the transmission activation signal after said predetermined transmission period has expired to thereby cause the transmitter to cease transmission of the telemetric signal.

12. An apparatus according to claim 1 wherein the tissue connector includes a porous surface of tissue compatible material into which tissue will develop.

13. An apparatus according to claim 1 wherein the tissue connector includes a reticulated layer of tissue compatible material into which tissue will develop.

14. An apparatus according to claim 1 wherein the capsule includes a convex upper surface which is deformable under force to cause activation of the force responsive sensor.

15. An apparatus according to claim 1 wherein the force responsive sensor is a deformable resilient structure having first and second contacts which are forced into electrical conductivity to cause activation of the force responsive sensor when the apparatus is forced due to mounting of the animal in which the apparatus is mounted.

16. An apparatus according to claim 1 wherein the capsule includes a concave lower surface that aids in the locating of the apparatus when after subcutaneous implantation in an animal.

17. An apparatus for detecting, analyzing and signaling estrus in a female animal which exhibits standing heat behavior, comprising:
a support;
a self-contained electrical power source connected to the support;
a force responsive sensor connected to the support with at least one outer flexible portion for changing in response to force and detecting force applied to the apparatus;
a controller connected to the support and electrically connected to receive electrical power from the self-contained electrical power source; said controller being connected to receive information from the force responsive sensor which is indicative of application of force to the force responsive sensor; said controller being capable of producing a transmission activation signal;
said controller further including a standing heat analyzer for analyzing and discriminating standing heat events from spurious mounting events; said standing heat analyzer comprising means for measuring duration of force detected by the force responsive sensor to determine mounting event duration and comparing the mounting event duration against a predetermined mounting event duration threshold;

said controller still further including an estrous analyzer for counting a plurality of standing heat events to control production of said transmission activation signal; said estrous analyzer including means for counting a plurality of standing heat events and comparing frequency of standing heat events against a predetermined standing heat event frequency threshold, to control production of said transmission activation signal;

a transmitter connected to said support and electrically connected to receive electrical power from said self-contained electrical power source; said transmitter being capable of producing a telemetric signal which can propagate from the apparatus; said transmitter being connected to receive said transmission activation signal from the controller to control production of the telemetric signal by the transmitter; and an antenna connected to the support and electrically connected to receive the telemetric signal from said transmitter and to broadcast the telemetric signal.

18. An apparatus according to claim 17 wherein said means for counting a plurality of standing heat events and comparing frequency of standing heat events against a predetermined standing heat event frequency threshold, determines frequency of standing heat events over a standing heat analysis period which advances with time.

19. An apparatus according to claim 17 wherein said means for measuring duration of force compares the duration of force detected by the force responsive sensor against a predetermined mounting event duration threshold equal to approximately 5 seconds or longer.

20. An apparatus according to claim 17 wherein said means for counting a plurality of standing heat events and comparing frequency of standing heat events against a predetermined standing heat event frequency threshold compares frequency of standing heat events against a standing heat event frequency threshold equal to at least 3 standing heat events within an 8 hour period.

21. An apparatus according to claim 17 wherein the force responsive sensor is a deformable resilient structure having first and second contacts which are forced into electrical conductivity to cause activation of the force responsive sensor when the apparatus is forced due to mounting of the animal bearing the apparatus.

22. A system for detecting, analyzing and signaling estrus in a female animal which exhibits standing heat behavior, comprising:
a subcutaneously implantable apparatus including:
a substantially fluid-tight capsule made of tissue compatible material suitable for surgical subcutaneous implantation in said animal;
a tissue connector connected to the capsule for aiding in attachment of the apparatus to tissue in said animal to thereby assist in maintaining the apparatus in a desired location under the hide of the animal;
a self-contained electrical power source mounted within the capsule;
a force responsive sensor connected to the capsule for detecting force applied thereto;
a controller mounted within the capsule and connected to receive electrical power from the self-contained electrical power source; said controller being connected to receive information from the force responsive sensor which is indicative of application of force to the force responsive sensor; said controller being capable of producing a transmission activation signal;
a transmitter mounted within said capsule and connected to receive electrical power from said self-contained electrical power source; said transmitter being capable of producing a telemetric signal which is capable of broadcast through the hide of said animal when the apparatus is implanted; said transmitter being connected to receive said transmission activation signal from the controller to control production of the telemetric signal by the transmitter; and
an antenna connected to the capsule and electrically connected to receive the telemetric signal from said transmitter and to broadcast the telemetric signal; and
a receiver remote from the implantable apparatus for receiving the telemetric signal as an indication that said animal has experienced behavior indicating estrus.

23. A system according to claim 22 and further comprising an estrous signal indicator connected to the receiver for indicating to a herdsman that the receiver has received a telemetric signal and that said animal has experienced behavior indicating estrus.

24. A system according to claim 22 and further comprising an estrous status data recorder connected to the receiver for recording information concerning receipt of the telemetric signal for said animal.

25. A system for detecting, analyzing and signaling estrus in a female animal which exhibits standing heat behavior, comprising:
an apparatus for connection to said animal, including:
a support;
a self-contained electrical power source connected to the support;
a force responsive sensor connected to the support with at least one outer flexible portion for changing in response to force and detecting force applied to the apparatus;
a controller connected to the support and electrically connected to receive electrical power from the self-contained electrical power source; said controller being connected to recieve information from the force response sensor which is indicative of application of force to the force responsive sensor; said controller being capable of producing a transmission activation signal;
said controller further including a standing heat analyzer for analyzing and discriminating standing heat events from spurious mounting events; said standing heat analyzer comprising means for measuring duration of force detected by the force responsive sensor to determine mounting event duration and comparing the mounting event duration against a predetermined mounting event duration threshold;
said controller still further including an estrous analyzer for counting a plurality of standing heat events to control production of said transmission activation signal; said estrous analyzer including means for counting a plurality of standing heat events and comparing frequency of standing heat events against a predetermined standing heat event frequency threshold, to control production of said transmission activation signal;

a transmitter connected to said support and electrically connected to receive electrical power from said self-contained electrical power source; said transmitter being capable of producing a telemetric signal which can propagate from the apparatus; said transmitter being connected to receive said transmission activation signal from the controller to control production of the telemetric signal by the transmitter;

an antenna connected to the support and electrically connected to receive the telemetric signal from said transmitter and to broadcast the telemetric signal; and a receiver remote from said apparatus for receiving the telemetric signal as an indication that said animal has experienced behavior indicating estrus.

26. A system according to claim 25 and further comprising an estrous signal indicator connected to the receiver for indicating to a herdsman that the receiver has received a telemetric signal and that said animal has experienced behavior indicating estrus.

27. A system according to claim 25 and further comprising an estrous status data recorder connected to the receiver for recording information concerning receipt of the telemetric signal for said animal.

28. A method for obtaining information indicative of estrus in a female animal which exhibits standing heat behavior, comprising:

surgically implanting an apparatus for detecting, analyzing and signaling estrus at a subcutaneous location on upper portions of said animal's hindquarters;

exposing said animal to other herd members;

sensing mounting of said animal by other herd members using said apparatus;

recording data in said apparatus indicative of mounting sensed in said sensing step;

controllably communicating a telemetric signal from said apparatus while implanted which is capable of indicating that said animal has experienced standing heat behavior indicative of estrus;

bringing said animal with implanted apparatus into proximity with a suitable receiver for receiving said telemetric signal from said apparatus while implanted;

receiving any telemetric signal controllably communicated from said apparatus implanted in said animal;

indicating estrus condition using an estrous signal indicator which is perceivable by a herdsman.

29. A method according to claim 28 and further comprising:

comparing duration of force detected by said apparatus to a predetermined mounting event duration threshold;

discriminating standing heat events which exceed said mounting event duration threshold from spurious mounting events;

counting a plurality of standing heat events;

determining frequency of standing heat events from said plurality of standing heat events;

comparing the frequency of standing heat events to a predetermined standing heat event frequency threshold;

communicating said telemetric signal if said frequency of standing heat events exceeds the predetermined standing heat event frequency threshold.

30. A method according to claim 29 wherein said mounting event duration threshold is approximately 5 seconds.

31. A method according to claim 29 wherein said standing heat event frequency threshold is at least 3 standing heat events within an 8 hour period.

32. A method according to claim 29 wherein said mounting event duration threshold is approximately 5 seconds, and said standing heat event frequency threshold is at least 3 standing heat events within and 8 hour period.

33. A method for obtaining information indicative of estrus in a female animal which exhibits standing heat behavior, comprising:

placing an apparatus for detecting, analyzing and signaling estrus at upper portions of said animal's hindquarters;

exposing said animal to other herd members;

comparing duration of force detected by said apparatus to a predetermined mounting event duration threshold;

discriminating standing heat events which exceed said mounting event duration threshold from spurious mounting events;

counting a plurality of standing heat events;

determining frequency of standing heat events from said plurality of standing heat events;

comparing the frequency of standing heat events to a predetermined standing heat event frequency threshold;

selectively emitting a telemetric signal if said frequency of standing heat events exceeds the predetermined standing heat event frequency threshold;

bringing said animal with said apparatus into proximity with a suitable receiver for receiving a telemetric signal from said apparatus which indicates that said animal has experienced standing heat behavior indicative of estrus;

receiving any telemetric signal from said apparatus;

producing an estrous signal indicator which is perceivable by a herdsman to thus indicate estrus.

34. A method according to claim 33 wherein said mounting event duration threshold is approximately 5 seconds.

35. A method according to claim 33 wherein said standing heat event frequency threshold is at least 3 standing heat events within an 8 hour period.

36. A method according to claim 33 wherein said mounting event duration threshold is approximately 5 seconds, and said standing heat frequency threshold is at least 3 standing heat events within and 8 hour period.

* * * * *